(12) United States Patent
Kim et al.

(10) Patent No.: US 8,530,059 B2
(45) Date of Patent: Sep. 10, 2013

(54) RED PHOSPHORESCENT COMPOUND AND ORGANIC ELECTROLUMINESCENT DEVICE USING THE SAME

(75) Inventors: Jung Keun Kim, Seoul (KR); Jeong Dae Seo, Incheon (KR); Hyun Cheol Jeong, Jinju-si (KR); Chun Gun Park, Seoul (KR); Jong Kwan Bin, Kyungki-do (KR); Kyung Hoon Lee, Seoul (KR); Sung Hoon Pieh, Seoul (KR)

(73) Assignee: LG Display Co., Ltd., Seoul (KR)

( * ) Notice: Subject to any disclaimer, the term of this patent is extended or adjusted under 35 U.S.C. 154(b) by 1381 days.

(21) Appl. No.: 11/593,147

(22) Filed: Nov. 6, 2006

(65) Prior Publication Data

US 2007/0104979 A1    May 10, 2007

(30) Foreign Application Priority Data

Nov. 7, 2005   (KR) .................. 10-2005-0105980

(51) Int. Cl.
*H01L 51/54* (2006.01)
*C09K 11/06* (2006.01)

(52) U.S. Cl.
USPC ...... 428/690; 428/917; 252/301.16; 313/504; 313/506; 257/40; 257/102; 257/E51.044; 546/10

(58) Field of Classification Search
None
See application file for complete search history.

(56) References Cited

U.S. PATENT DOCUMENTS

2003/0072964 A1  4/2003  Kwong et al. .............. 428/690
2004/0127710 A1  7/2004  Park et al. .................. 546/2

FOREIGN PATENT DOCUMENTS

WO   WO 03/040256 A2 *  5/2003

OTHER PUBLICATIONS

European Search Report dated Mar. 6, 2007.

* cited by examiner

*Primary Examiner* — Michael H Wilson
(74) *Attorney, Agent, or Firm* — Morgan, Lewis & Bockius LLP

(57) ABSTRACT

Disclosed herein is a red phosphorescent compound of the following Formula 1:

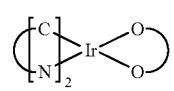

(1)

wherein

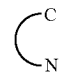

is includes a phenyl part and a quinoline part, the quinoline part has one substituent selected from a $C_1$-$C_4$ alkoxy group and the phenyl part has substituents independently selected from hydrogen, $C_1$-$C_4$ alkyl groups and $C_1$-$C_4$ alkoxy groups, and

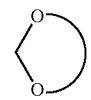

is selected from 2,4-pentanedione, 2,2,6,6-tetramethylheptane-3,5-dione, 1,3-propanedione, 1,3-butanedione, 3,5-heptanedione, 1,1,1-trifluoro-2,4-pentanedione, 1,1,1,5,5,5-hexafluoro-2,4-pentanedione, and 2,2-dimethyl-3,5-hexanedione.

4 Claims, 2 Drawing Sheets

CuPC

NPD (btp)$_2$Ir(acac)

BAlq

Alq$_3$

CBP

RED PHOSPHORESCENT COMPOUND AND ORGANIC ELECTROLUMINESCENT DEVICE USING THE SAME

This application claims the benefit of Korean Patent Application No. 10-2005-0105980 filed on Nov. 7, 2005, which is hereby incorporated by reference as if fully set forth herein.

BACKGROUND OF THE INVENTION

1. Field of the Invention

The present invention relates to a red light-emitting phosphorescent compound (hereinafter, referred to simply to as a 'red phosphorescent compound') and an organic electroluminescent (EL) device using the same. More particularly, the present invention relates to a red phosphorescent compound, and an organic electroluminescent device comprising a laminate of an anode, a light-emitting layer and a cathode wherein the red phosphorescent compound is used as a dopant of the light-emitting layer.

2. Discussion of the Related Art

With recent trends toward large-area displays, there has been increased demand for flat display devices that take up little space. In particular, technology of organic electroluminescent (EL) devices (also termed 'organic light emitting diodes (OLEDs)') as flat display devices has been rapidly developed. A variety of prototypes of organic electroluminescent (EL) devices have been reported to date.

When charge carriers are injected into an organic film formed between an electron injecting electrode (cathode) and a hole injecting electrode (anode) of an organic electroluminescent device, electrons combine with holes to create electron-hole pairs, which then decay to emit light. Organic electroluminescent devices have advantages in that they can be fabricated on flexible transparent substrates (e.g., plastic substrates) and can be operated at a voltage (e.g., 10V or below) lower than voltages required to operate plasma display panels (PDPs) and inorganic electroluminescent devices. Other advantages of organic electroluminescent devices are relatively low power consumption and excellent color representation. Further, since organic electroluminescent (EL) devices can emit light of three colors (i.e., green, blue and red), they have been the focus of intense interest lately as next-generation display devices capable of producing images of various colors. A general method for fabricating organic EL devices will be briefly explained below.

(1) First, a transparent substrate is covered with an anode material. Indium tin oxide (ITO) is generally used as the anode material.

(2) A hole injecting layer (HIL) is formed to a thickness of 10 to 30 nm on the anode. Copper (II) phthalocyanine (CuPc) is mainly used as a material of the hole injecting layer.

(3) A hole transport layer (HTL) is introduced into the resulting structure. The hole transport layer is formed by depositing 4,4'-bis[N-(1-naphthyl)-N-phenylamino]-biphenyl (NPB) to a thickness of about 30 to about 60 nm on the hole injecting layer.

(4) An organic light-emitting layer is formed on the hole transport layer. If necessary, a dopant may be added to a material for the organic light-emitting layer. For green light emission, tris(8-hydroxyquinoline)aluminum ($Alq_3$) as a material for the organic light-emitting layer is deposited to a thickness of about 30 to about 60 nm on the hole transport layer, and N-methylquinacridone (MQD) is mainly used as the dopant.

(5) An electron transport layer (ETL) and an electron injecting layer (EIL) are sequentially formed on the organic light-emitting layer. Alternatively, an electron injecting/transport layer is formed on the organic light-emitting layer. In the case of green light emission, since $Alq_3$ has excellent electron-transport ability, the formation of the electron injecting/transport layer may be unnecessary.

(6) A cathode material is coated on the electron injecting layer, and finally a passivation film is covered thereon.

The type of the organic electroluminescent devices (i.e. blue, green and red light-emitting devices) will be determined depending on the kind of materials for the light-emitting layer.

In the light-emitting layer, holes injected from the anode are recombined with electrons injected from the cathode to form excitons. Singlet excitons and triplet excitons are involved in the fluorescence and phosphorescence processes, respectively. Fluorescent materials using triplet excitons, which are involved in the phosphorescence process, whose probability of formation is 75%, exhibit high luminescence efficiency, as compared to fluorescent materials using singlet excitons whose probability of formation is 25%. In particular, the luminescence efficiency of red phosphorescent materials is considerably high, compared to that of fluorescent materials. Accordingly, a number of studies associated with the use of red phosphorescent materials in organic electroluminescent devices are being made to enhance the luminescence efficiency of the organic electroluminescent devices.

Phosphorescent materials for use in organic EL devices must satisfy the requirements of high luminescence efficiency, high color purity and long luminescence lifetime. As shown in FIG. 1, as the color purity of an organic EL device using a red phosphorescent material becomes higher (i.e. as the x-values on CIE chromaticity coordinates increase), the spectral luminous efficacy of the organic EL device decreases, making it difficult to achieve high luminescence efficiency of the organic EL device.

Thus, there is a demand to develop a red phosphorescent compound that exhibit desirable chromaticity coordinate characteristics (CIE color purity $X \geq 0.65$), high luminescence efficiency, and long luminescence lifetime.

SUMMARY OF THE INVENTION

Accordingly, the present invention is directed to a red phosphorescent compound and an organic electroluminescent (EL) device using the same that substantially obviate one or more problems due to limitations and disadvantages of the related art.

An object of the present invention is to provide a compound of Formula 1 that follows.

Another object of the present invention is to provide an organic electroluminescent (EL) device with high color purity, high luminance and long lifetime which uses one of the compounds as a dopant of a light-emitting layer.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, there is provided a red phosphorescent compound of Formula 1:

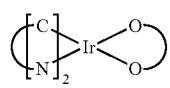
wherein
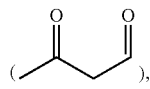
is
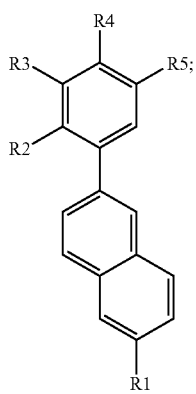
R1 is a $C_1$-$C_4$ alkoxy group; R2, R3, R4 and R5 are independently selected from hydrogen, $C_1$-$C_4$ alkyl groups and $C_1$-$C_4$ alkoxy groups; and
is selected from 2,4-pentanedione
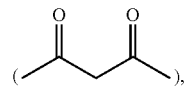
2,2,6,6-tetramethylheptane-3,5-dione
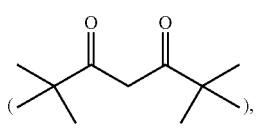
1,3-propanedione
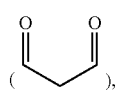
1,3-butanedione
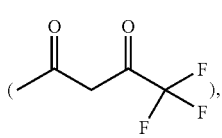
3,5-heptanedione
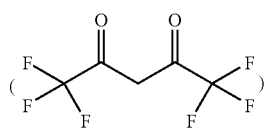 [SMILES: O=C(CC(=O)C(F)(F)F)C(F)(F)F]
1,1,1-trifluoro-2,4-pentanedione
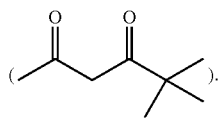
1,1,1,5,5,5-hexafluoro-2,4-pentanedione
and 2,2-dimethyl-3,5-hexanedione
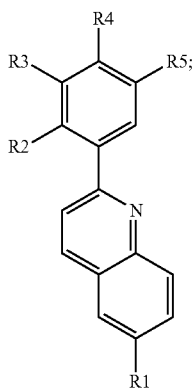
wherein
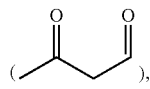
is R1 is a $C_1$-$C_4$ alkoxy group; R2, R3, R4 and R5 are independently selected from hydrogen, $C_1$-$C_4$ alkyl groups and $C_1$-$C_4$ alkoxy groups; and
is selected from 2,4-pentanedione
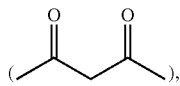
2,2,6,6-tetramethylheptane-3,5-dione
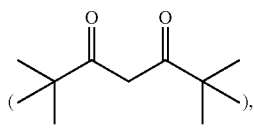
1,3-propanedione
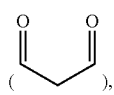
1,3-butanedione
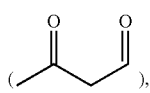
3,5-heptanedione
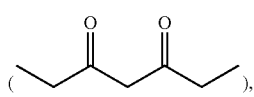
1,1,1-trifluoro-2,4-pentanedione
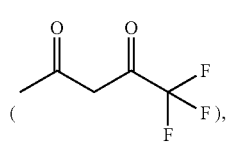
1,1,1,5,5,5-hexafluoro-2,4-pentanedione
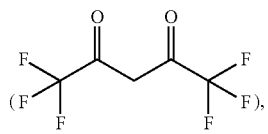
and 2,2-dimethyl-3,5-hexanedione
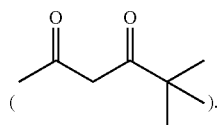
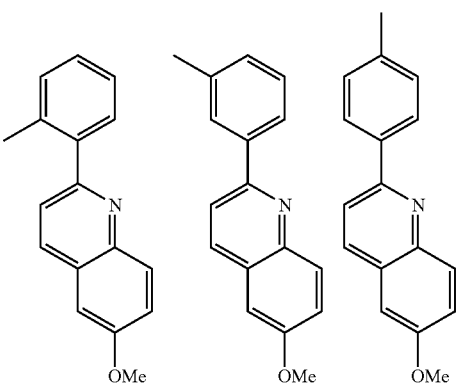
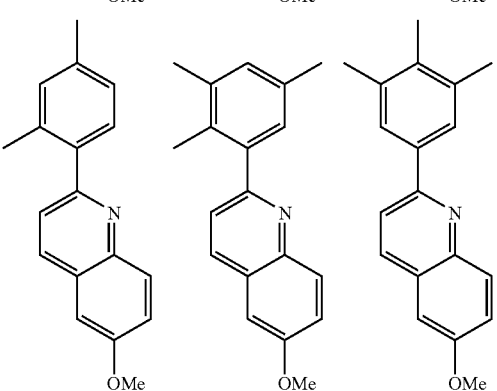

-continued
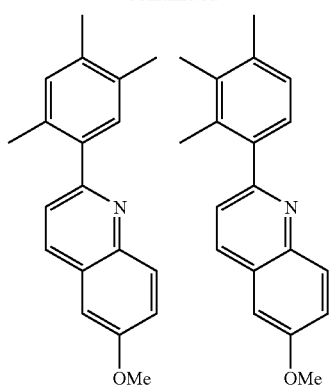
Examples of preferred compounds that can be represented by Formula 1 include the following compounds:
A-1
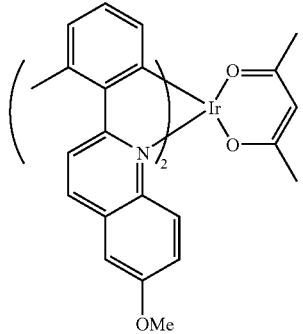
A-2
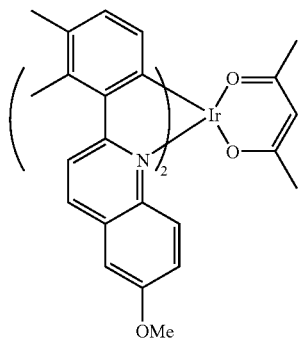
A-3
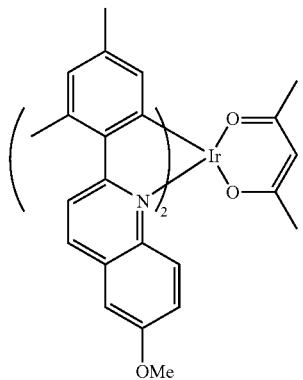
A-4
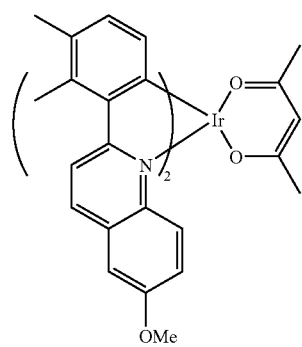
A-5
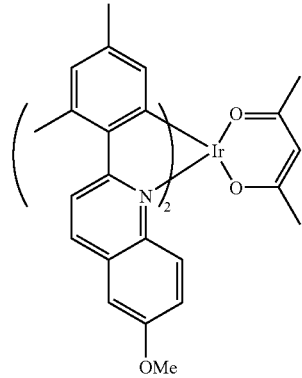
A-6
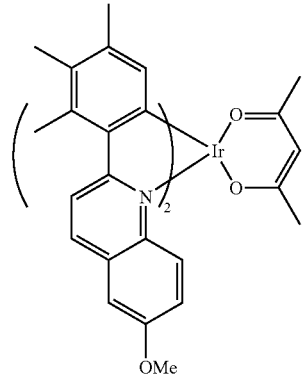
A-7
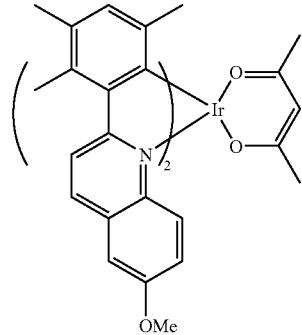

A-8 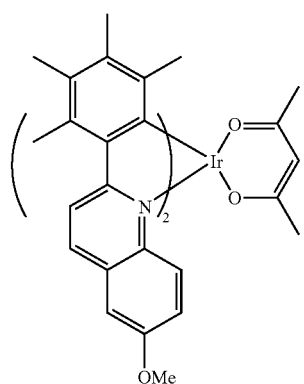
B-1 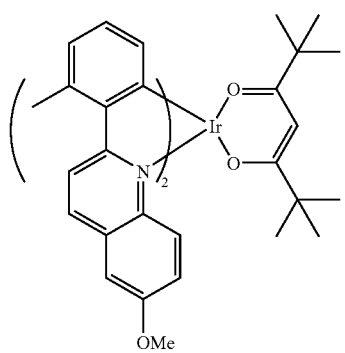
A-9 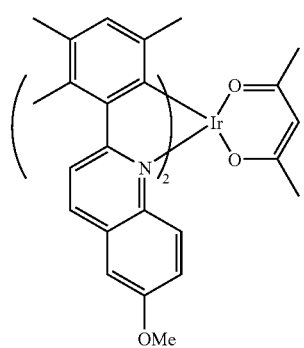
B-2 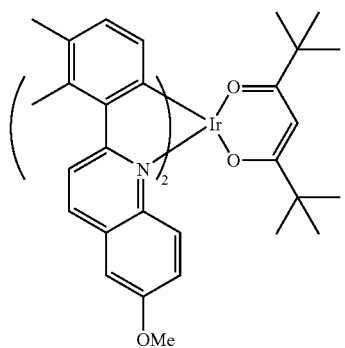
A-10 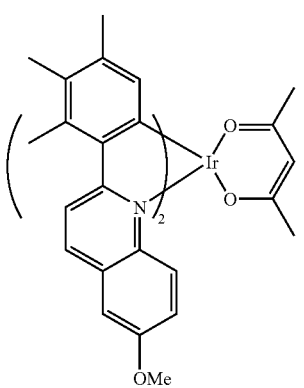
B-3 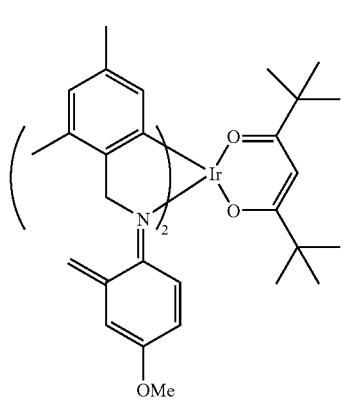
A-11 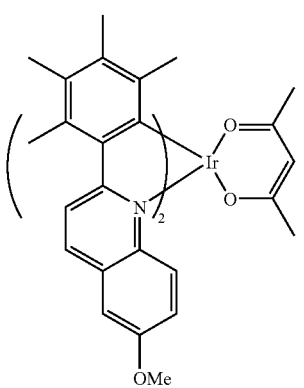
B-4 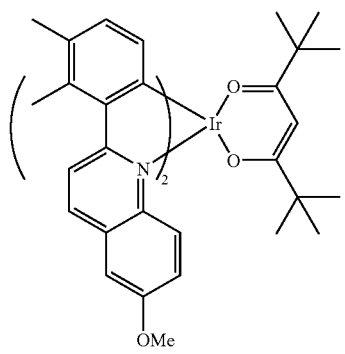

B-5 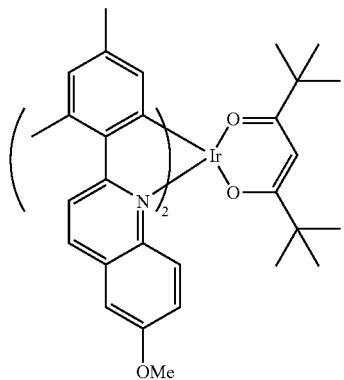

B-6 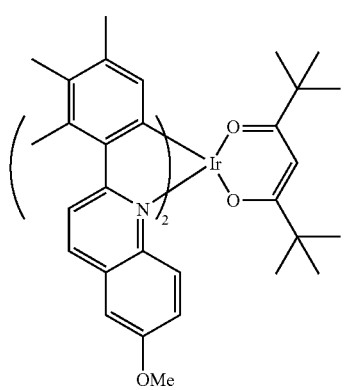

B-7 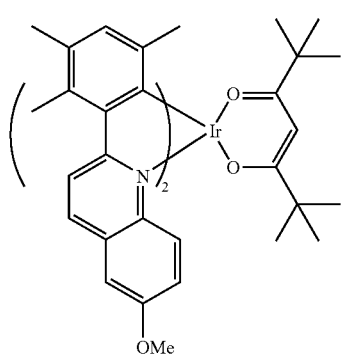

B-8 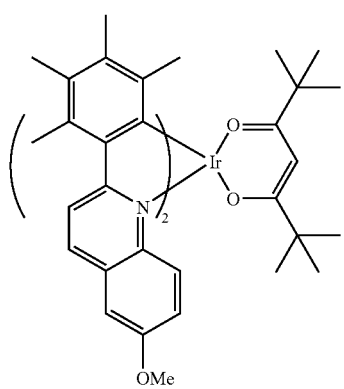

B-9 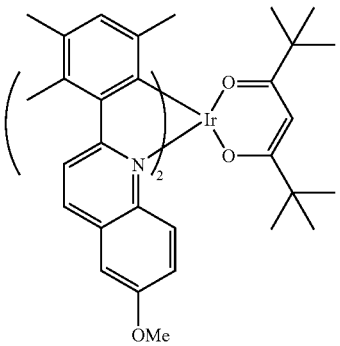

B-10 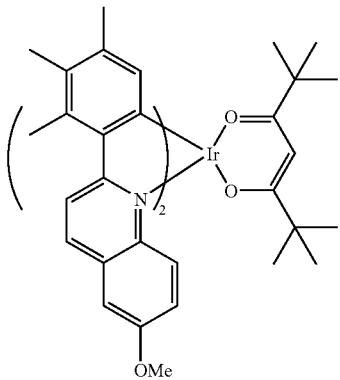

B-11 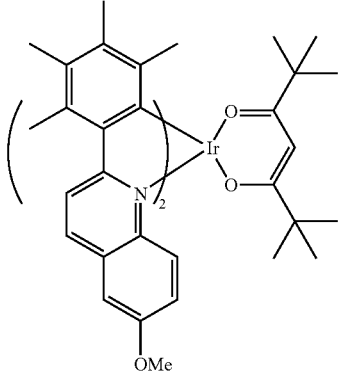

In yet another aspect of the present invention, there is provided an organic electroluminescent (EL) device comprising an anode, a hole injecting layer (HIL), a hole transport layer (HTL), an light-emitting layer, an electron transport layer (ETL) and an electron injecting layer (EIL), and a cathode laminated in this order wherein the red phosphorescent compound of Formula 1 is used as a dopant of the light-emitting layer.

A host used in the light-emitting layer of the organic EL device according to the present invention may be selected from Al complexes, Zn complexes, and carbazole derivatives. The dopant may be preferably used in an amount of 0.5 to 20% by weight, based on the weight of the host. When the dopant is used within this range, the desired effects of the organic EL device can be achieved. The Al and Zn complexes may have at least one ligand selected from quinolyl, biphenyl, isoquinolyl, phenyl, naphthyl, methylquinolyl, dimethylquinolyl and dimethylisoquinolyl groups. The carbazole derivatives may be preferably 4,4'-N,N' dicarbazole biphenyl (CBP).

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Figure 1:
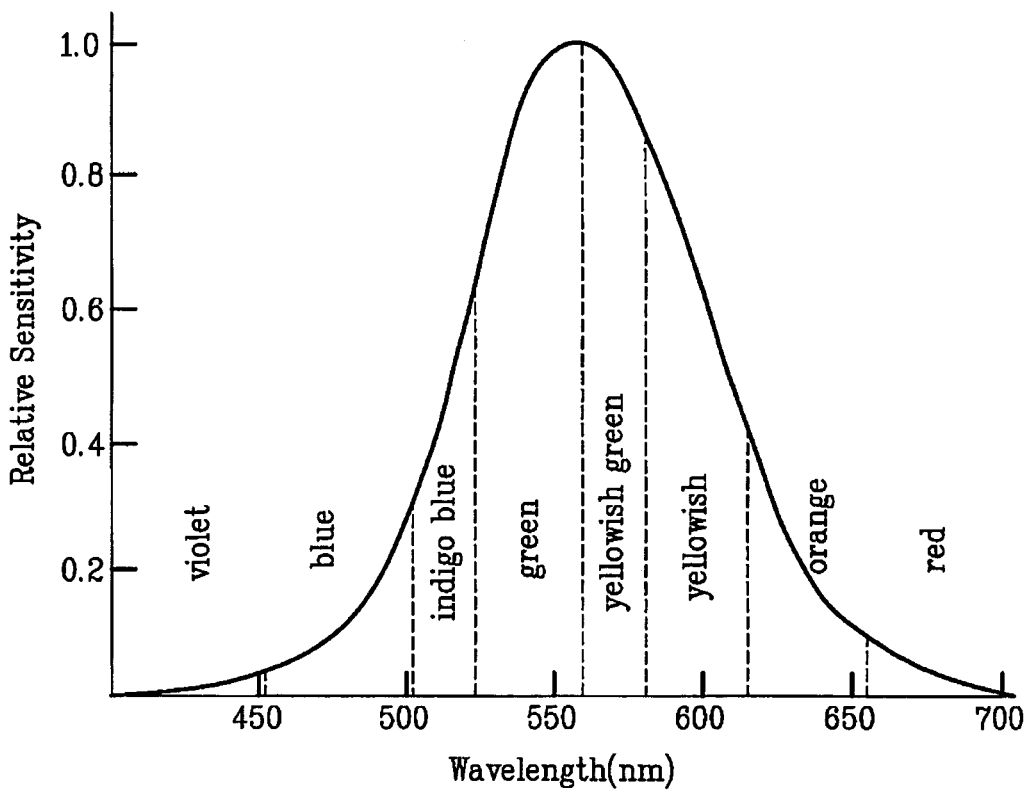
FIG. 1 shows a graph showing a phenomenon wherein the color purity of an organic EL device becomes higher (i.e. as the x-values on CIE chromaticity coordinates increase), the relative sensitivity of the organic EL device decreases.
Figure 2:
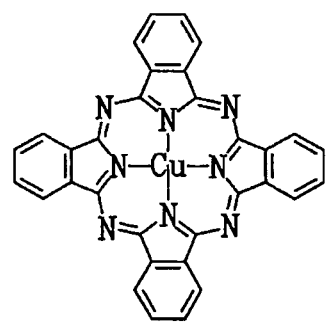
FIG. 2 shows the structural formulas of NPB, copper (II) phthalocyanine (CuPc), (btp)$_2$Ir(acac), Alq$_3$, BAlq and CBP used in Example Section according to the present invention.
Figure 2:
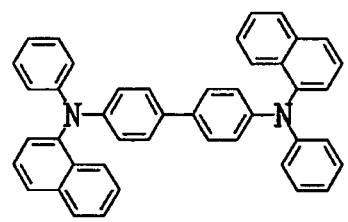
Figure 2:
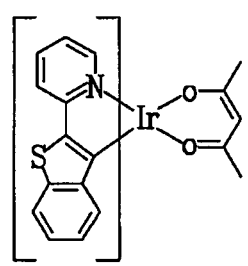
Figure 2:
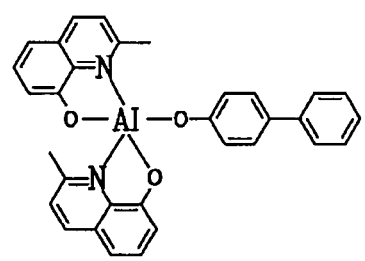
Figure 2:
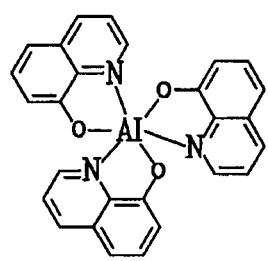
Figure 2:
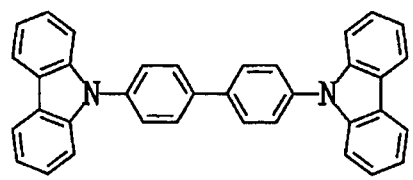

Reference will now be made in detail to the preferred embodiments of the present invention associated with a red phosphorescent compound and an organic electroluminescent (EL) device using the red phosphorescent compound according to the present invention, examples of which are illustrated in the annexed drawings.

Hereinafter, a method for synthesizing iridium (III) (2-(3-methylphenyl)-6-methoxyquinolinato-N,C$^{2'}$)(2,4-pentanedionate-O,O) ("A-2"), which is a red phosphorescent compound represented by Formula 1, for use in an organic electroluminescent device.

SYNTHESIS EXAMPLES

1. Synthesis of 2-(3-methylphenyl)-6-methoxyquinoline

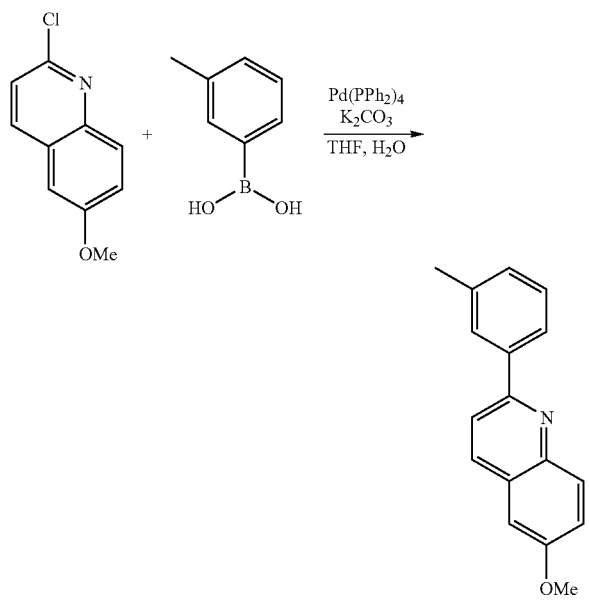

3-Methylphenyl borate (1.3 mmol), 2-chloro-6-methoxyquinoline (1 mmol), tetrakis(triphenylphosphine) palladium (O) (0.05 mmol) and potassium carbonate (3 mmol) were dissolved in THF (30 mL) and H$_2$O (10 mL). The resulting solution was stirred in a bath at 100° C. for 24 hours. After completion of the reaction, the solvents were removed. The reaction mixture was extracted with dichloromethane and water and distilled under reduced pressure. The resulting residue was purified by silica gel column chromatography. The eluate was distilled under reduced pressure. The residue was recrystallized from dichloromethane and petroleum ether, and filtered to yield 2-(3-methylphenyl)-6-methoxyquinoline as a solid.

2. Synthesis of Dichloro-Crosslinked Dimer Complex

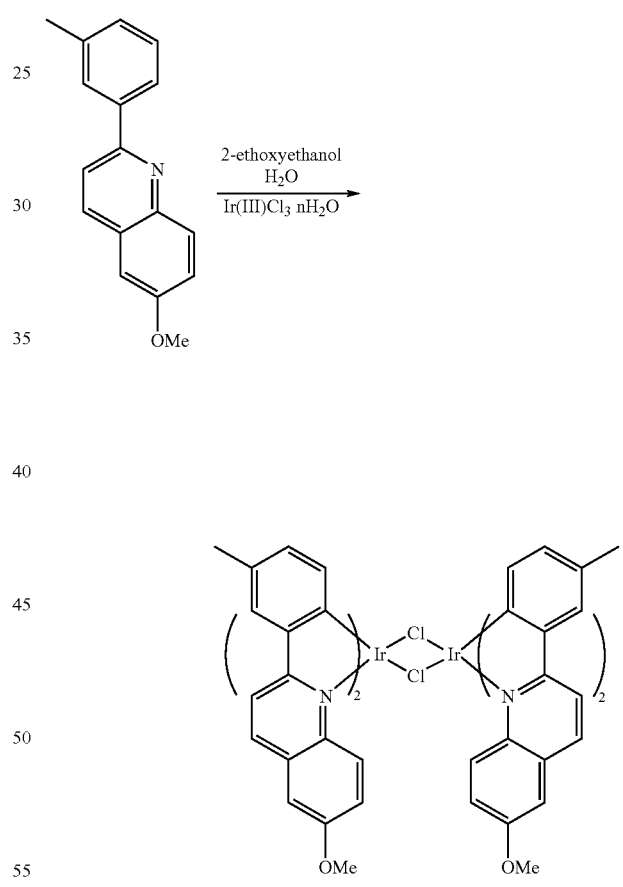

Iridium (III) chloride hydrate (1 mmol), the 2-(3-methylphenyl)-6-methoxyquinoline (2.5 mmol) and a mixed solvent (30 mL) of 2-ethoxyethanol and distilled water (3:1 (v/v)) were put in a dried two-neck round-bottom flask. After the mixture was refluxed for 24 hours, water was added thereto to obtain a solid. The solid was filtered and washed with methanol and petroleum ether to yield the dichloro-crosslinked dimer complex.

3. Synthesis of iridium (III) (2-(3-methylphenyl)-6-methoxyquinolinato-N,C$^{2'}$)(2,4-pentanedionate-O,O)

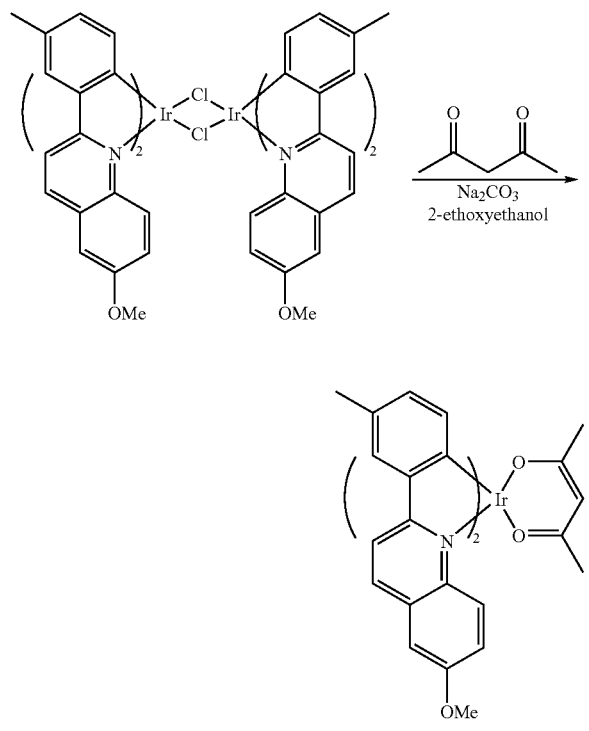

The dichloro-crosslinked dimer complex (1 mmol), 2,4-pentanedione (3 mmol), sodium carbonate (Na$_2$CO$_3$) (6 mmol) and 2-ethoxyethanol (30 mL) were put in a dried two-neck round-bottom flask. Then, the mixture was refluxed for 24 hours. The reaction mixture was allowed to cool to room temperature, and then distilled water was added thereto to obtain a solid. The solid was filtered and dissolved in dichloromethane. The solution was filtered through silica gel. The solvent was distilled off under reduced pressure and the resulting residue was washed with methanol and petroleum ether to yield iridium (III) (2-(3-methylphenyl)-6-methoxyquinolinato-N,C$^{2'}$)(2,4-pentanedionate-O,O).

Hereinafter, a detailed description will be made of preferred examples of the present invention. The invention is not to be construed as being limited to the examples.

EXAMPLES

Example 1

An ITO-coated glass substrate was patterned to have a light-emitting area of 3 mm×3 mm, followed by cleaning. After the patterned substrate was disposed in a vacuum chamber, the standard pressure of the chamber was adjusted to 1×10$^{-6}$ torr. CuPc (200 Å), NPD (400 Å), BAlq+A-2 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,052 cd/m$^2$ at an electric current of 0.9 mA and a voltage of 6.5 V. At this time, the CIE chromaticity coordinates were x=0.648 and y=0.349. The lifetime (defined as the time taken before the luminance of the organic EL device decreases to half its initial value) of the organic EL device was 4,300 hours at 2,000 cd/m$^2$.

Example 2

An ITO-coated glass substrate was patterned to have a light-emitting area of 3 mm×3 mm, followed by cleaning. After the patterned substrate was disposed in a vacuum chamber, the standard pressure of the chamber was adjusted to 1×10$^{-6}$ torr. CuPc (200 Å), NPD (400 Å), BAlq+A-6 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,095 cd/m$^2$ at an electric current of 0.9 mA and a voltage of 6.2 V. At this time, the CIE chromaticity coordinates were x=0.651 and y=0.337. The lifetime (defined as the time taken before the luminance of the organic EL device decreases to half its initial value) of the organic EL device was 4,500 hours at 2,000 cd/M$^2$.

Example 3

An ITO-coated glass substrate was patterned to have a light-emitting area of 3 mm×3 mm, followed by cleaning. After the patterned substrate was disposed in a vacuum chamber, the standard pressure of the chamber was adjusted to 1×10$^{-6}$ torr. CuPc (200 Å), NPD (400 Å), BAlq+A-7 (7%) (200 Å), Alq$_3$ (300 Å), LiF (5 Å) and Al (1000 Å) were sequentially deposited on the ITO glass substrate to fabricate an organic EL device.

The luminance of the organic EL device was 938 cd/m$^2$ at an electric current of 0.9 mA and a voltage of 5.3 V. At this time, the CIE chromaticity coordinates were x=0.652 and y=0.344. The lifetime (defined as the time taken before the luminance of the organic EL device decreases to half its initial value) of the organic EL device was 4,200 hours at 2,000 cd/M$^2$.

Comparative Example 1

An ITO-coated glass substrate was patterned to have a light-emitting area of 3 mm×3 mm, followed by cleaning. The patterned substrate was disposed in a vacuum chamber. Then, the standard pressure of the chamber was adjusted to 1×10$^{-6}$ torr. CuPc (200 Å), NPD (400 Å), BAlq+(btp)$_2$Ir(acac) (7%) (200 Å), Alq$_3$ (300 Å), LiF (5 Å) and Al (1000 Å) were sequentially deposited on the ITO glass substrate to manufacture an organic EL device.

The luminance of the organic EL device was 780 cd/m$^2$ at an electric current of 0.9 mA and a voltage of 7.5 V. At this time, the CIE chromaticity coordinates were x=0.659 and y=0.329. The lifetime (defined as the time taken before the luminance of the organic EL device decreases to half its initial value) of the organic EL device was 2,500 hours at 2,000 cd/m$^2$.

The organic EL devices fabricated in Examples 1 to 5 and Comparative Example 1 were evaluated for efficiency, CIE chromaticity coordinates, luminance and lifetime characteristics. The results are shown in Table 1.

TABLE 1

| Device | Voltage (V) | Electric current (mA) | Luminance (cd/m$^2$) | Current efficiency (cd/A) | Power efficiency (lm/W) | CIE (X) | CIE (Y) | Life time (h) (half the initial luminance) |
|---|---|---|---|---|---|---|---|---|
| Ex. 1 | 5.6 | 0.9 | 1,358 | 13.58 | 7.61 | 0.648 | 0.349 | 4,300 |
| Ex. 2 | 5.7 | 0.9 | 1,423 | 14.23 | 7.84 | 0.651 | 0.337 | 4,500 |
| Ex. 3 | 6.1 | 0.9 | 1,501 | 15.01 | 7.73 | 0.652 | 0.342 | 4,200 |
| Comp. Ex. 1 | 7.5 | 0.9 | 780 | 7.8 | 3.3 | 0.659 | 0.329 | 2,500 |

What is claimed is:

1. A red phosphorescent compound of one of Formula 1 below:

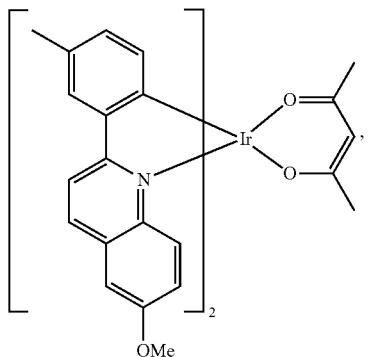

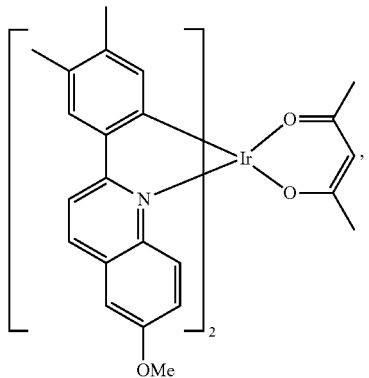

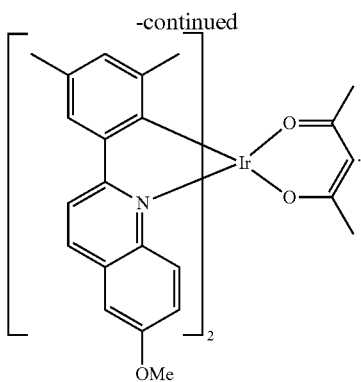

2. An organic electroluminescent (EL) device comprising an anode,
a hole injecting layer,
a hole transport layer,
a light-emitting layer,
an electron transport layer,
an electron injecting layer, and
a cathode laminated in this order
wherein the red phosphorescent compound according to claim 1 is used as a dopant of the light-emitting layer and is present in an amount of 0.5 to 20% by weight, based on the weight of a host.

3. The organic electroluminescent (EL) device according to claim 2, wherein the host is selected from an Al complex, a Zn complex, and a carbazole derivative.

4. The organic electroluminescent (EL) device according to claim 3, wherein the Al or Zn complex has at least one ligand selected from quinolyl, biphenyl, isoquinolyl, phenyl, naphthyl, methylquinolyl, dimethylquinolyl and dimethyl-isoquinolyl groups, and the carbazole derivative is 4,4'-N,N' dicarbazole biphenyl (CBP).

* * * * *